United States Patent
Liu et al.

(10) Patent No.: US 10,576,499 B2
(45) Date of Patent: Mar. 3, 2020

(54) ULTRASONIC PHASED ARRAY PROBE USING PCB AS MATCHING LAYER

(71) Applicants: Sheng Liu, State College, PA (US); Ronald Keller, Port Matilda, PA (US)

(72) Inventors: Sheng Liu, State College, PA (US); Ronald Keller, Port Matilda, PA (US)

(73) Assignee: Olympus Scientific Solutions Americas Inc., Waltham, MA (US)

( * ) Notice: Subject to any disclaimer, the term of this patent is extended or adjusted under 35 U.S.C. 154(b) by 399 days.

(21) Appl. No.: 15/445,479

(22) Filed: Feb. 28, 2017

(65) Prior Publication Data

US 2017/0246663 A1     Aug. 31, 2017

Related U.S. Application Data

(60) Provisional application No. 62/301,115, filed on Feb. 29, 2016.

(51) Int. Cl.

| | |
|---|---|
| *B06B 1/06* | (2006.01) |
| *H05K 1/03* | (2006.01) |
| *H01L 41/22* | (2013.01) |
| *H01L 41/09* | (2006.01) |
| *H05K 1/02* | (2006.01) |
| *H05K 1/11* | (2006.01) |
| *G01N 29/24* | (2006.01) |
| *G01N 29/32* | (2006.01) |
| *G01N 29/26* | (2006.01) |

(52) U.S. Cl.
CPC ......... *B06B 1/0622* (2013.01); *G01N 29/245* (2013.01); *G01N 29/262* (2013.01); *G01N 29/32* (2013.01); *H05K 1/028* (2013.01); *H05K 1/03* (2013.01); *H05K 1/111* (2013.01); *H05K 2201/0104* (2013.01)

(58) Field of Classification Search
CPC .. B06B 1/0622; G01N 29/245; G01N 29/262; G01N 29/32; H05K 1/028; H05K 1/111; H05K 2201/0104
USPC .................................................. 310/322, 334
See application file for complete search history.

(56) References Cited

U.S. PATENT DOCUMENTS

| | | | | |
|---|---|---|---|---|
| 5,894,646 A | * | 4/1999 | Hanafy | B06B 1/0629 29/25.35 |
| 2006/0241468 A1 | * | 10/2006 | Lu | B06B 1/0622 600/459 |
| 2009/0156940 A1 | * | 6/2009 | Yen | B06B 1/0633 600/459 |
| 2017/0080255 A1 | * | 3/2017 | Law | G01S 7/521 |

* cited by examiner

*Primary Examiner* — Thomas M Dougherty
(74) *Attorney, Agent, or Firm* — Gerald P. Kazanjian

(57) ABSTRACT

Disclosed is a flexible ultrasonic transducer in which a single layer serves dual function as both a matching layer and a flexible circuit for making electrical connections, and there is no separate matching layer. Also disclosed is a method of assembling the flexible transducer.

22 Claims, 5 Drawing Sheets

ULTRASONIC PHASED ARRAY PROBE USING PCB AS MATCHING LAYER

CROSS-REFERENCE TO RELATED APPLICATIONS

This application claims the benefit and priority of U.S. Provisional patent application Ser. No. 62/301,115 filed Feb. 29, 2016 entitled FLEXIBLE ARRAY USING A FLEXIBLE CIRCUIT AS THE MATCHING LAYER, the entire disclosure of which is incorporated herein by reference.

FIELD OF THE INVENTION

The invention relates to manufacture of flexible ultrasonic probe array transducers for non-destructive testing/inspection (NDT/NDI), more specifically to an ultrasonic phased array probe using a printed circuit board (PCB) directly as its matching layer.

BACKGROUND OF THE INVENTION

Flexible probe array transducers are commonly used for ultrasonic inspection of tubes, pipes or other curved surfaces. The flexible array often comprises a long ribbon-like acoustic module which is wrapped around the tube or pipe for detecting, for example, thickness variation in tubes, and/or cracks in pipes or welds.

The acoustic module usually comprises four layers: a composite piezoelectric array (hereinafter, the "composite"), a flexible printed circuit board (hereinafter, the "flexible circuit"), a backing material and a matching layer. The composite comprises multiple piezoelectric elements for transmitting and receiving ultrasonic energy. Each element of the composite is electrically contacted by a conductive layer, usually gold, and the flexible circuit is commonly used to conveniently route all electrical contacts to a suitable connector. The purpose of the backing material is to ensure that the acoustic module emits ultrasonic energy from one side only and to dampen the resonance of the elements. When the elements are well damped, shorter pulses of ultrasonic energy may be emitted. The matching layer is required on the emitting side of the acoustic module to ensure efficient transmission of ultrasonic energy from the composite into the material being inspected, and to prevent unwanted reflections so that the emitted signal can have shorter pulse width and larger bandwidth.

FIG. 1A is a schematic illustration of an acoustic module in existing practice, showing the four layers described in the previous paragraph. The acoustic module in existing practice has a number of problems and disadvantages. A first problem is related to the number of layers and the number of steps in the manufacturing process, both of which lead to high cost and long manufacturing lead times. In addition, the large number of layers impacts reliability of the final product because failure of glue joints between layers is a commonly known reliability problem.

A further problem with the acoustic module in existing practice is that the presence of the flexible circuit results in a lack of intimate contact between the composite and the backing material. This lack of intimate contact reduces the effectiveness of the backing material, resulting in increased ringing during ultrasonic emission and consequent loss of near-surface resolution.

SUMMARY OF THE INVENTION

Accordingly, it is a general objective of the present disclosure to mitigate the problems with existing acoustic modules.

It is a further objective of the present disclosure to reduce the number of layers from four to three, thereby simplifying the manufacturing process, reducing cost and improving product reliability.

It is a further objective of the present disclosure to bond the backing layer directly to the composite with the two layers in intimate contact, thereby reducing ring-down, improving near-surface resolution and enabling the user to detect flaws closer to the surface of the part being inspected.

It is a further objective of the present disclosure to have a simplified and robust manufacturing method which enhances the manufacturability, reliability and utility of the final product.

According to the present disclosure, the number of layers of the acoustic module is reduced by eliminating the separate matching layer of existing practice, and instead using a layer which combines the functions of both flexible circuit, preferably in the form of a PCB, and matching material.

DETAILED DESCRIPTION OF PREFERRED EMBODIMENT

It should be noted that, unlike existing practice, the assembly steps described in connection with FIGS. 3~5 below do not include a separate matching layer within acoustic module 2. This is an important and innovative aspect of the present invention. The difference between existing practice and the present invention is further highlighted in FIGS. 1A and 1B.

Figure 1A:
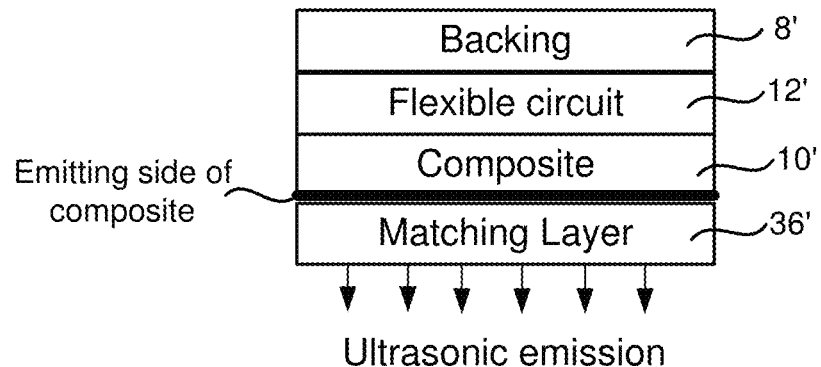
FIG. 1A is a schematic diagram of the layers comprising an acoustic module in existing practice.

FIG. 1A schematically shows existing practice, in which there are four separate layers. A composite 10' is attached to a flexible circuit 12' on the non-emitting side of composite 10'. A backing material 8' is then attached to flexible circuit 12' to prevent emission from that side of the acoustic module and to damp the ultrasonic elements. A separate matching layer 36' is attached to the emitting side of composite 10' to prevent unwanted reflections.

Figure 1B:
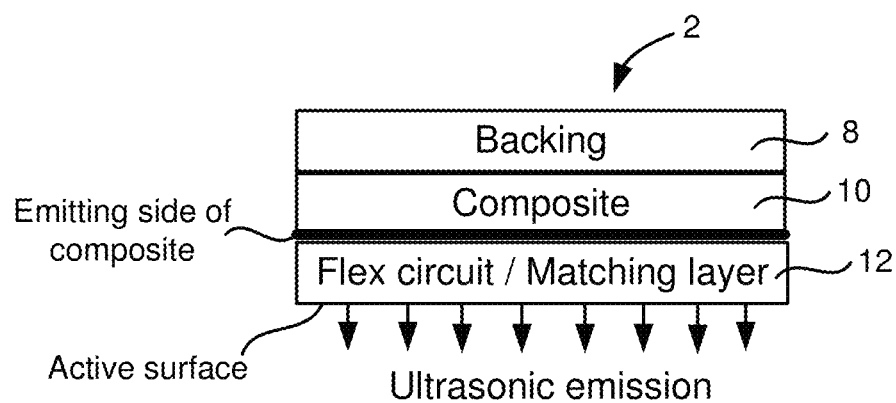
FIG. 1B is a schematic diagram of the layers comprising an acoustic module according to the present disclosure.

In contrast, as shown schematically in FIG. 1B, an acoustic module 2 according to the present disclosure comprises only three separate layers. Unlike existing practice, a composite 10 has a backing material 8 attached directly to and in intimate contact with its non-emitting side. In addition, and also unlike existing practice, a flexible circuit 12 is attached to the emitting side of composite 10, and there is no separate matching layer. In fact, flexible circuit 12 serves the dual function of providing electrical connections to composite 10 and providing the functions of a matching layer, namely preventing unwanted reflections. The material of flexible circuit 12 is preferably polyimide, whose properties include both acoustic impedance and acoustic velocity suitable for use as a matching layer. The inventors of the present invention have utilized this property to conceive a novel manufacture of an acoustic module in which the functions of flexible circuit and matching material are combined in a single layer. However, materials other than polyimide for flexible circuit 12 are also within the scope of the present disclosure. Any insulating material having acoustic impedance in the range from 2.5 to 7.5 MRayls may be suitable for flexible circuit 12.

Although not shown in FIG. 1B, it should be appreciated by those skilled in the art that the printed circuit board 12 can be coated or layered with a protective material at the bottom, providing enough toughness for probe (acoustic module) 2 to be moved over the testing surface, which often is rough and tough.

Acoustic module 2 has an active surface to be coupled with the testing surface during inspection, and comprises a sheet of printed circuit board, of which one surface is the active surface, the other surface having at least one printed circuit printed thereon, a layer of piezoelectric ceramic composite having an emitting side and a non-emitting side, with the emitting side abutting the printed circuit board, and a layer of backing material abutting the non-emitting side of the layer of ceramic composite, wherein all the layers of components are bonded together to form an acoustic laminated assembly, the printed circuit board and piezoelectric ceramic composite are connected, and the printed circuit board is further electrically coupled with at least one cable, and the printed circuit board is made out of material with acoustic impedance in the range from 2.5 to 7.5 MRayls.

Figure 2:
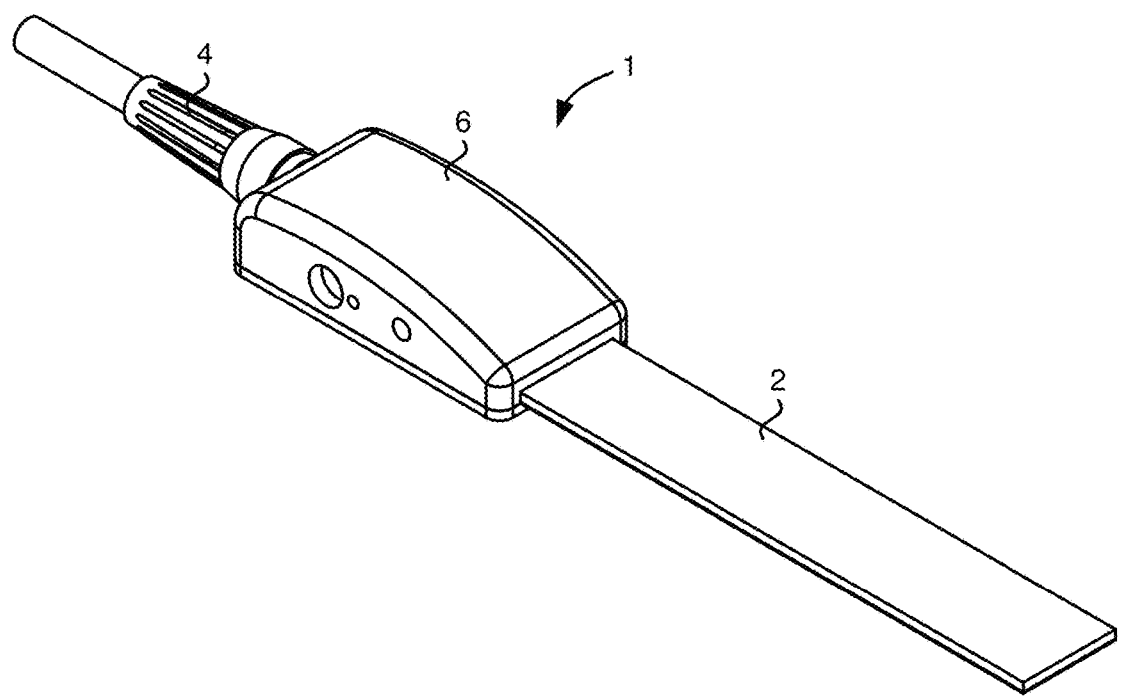
FIG. 2 is a perspective diagram of a flexible probe array assembly according to the present disclosure.

FIG. 2 is a perspective diagram of a flexible probe array assembly 1 according to the present invention. Acoustic module 2 is configured to transmit and receive ultrasonic energy and is shaped in a ribbon-like geometry which is convenient for wrapping around the outside of pipes or tubes for NDT/NDI. A cable assembly 4 comprises multiple shielded conductors 22 (See FIG. 5B) for connection to external electronic circuitry (not shown) which controls the ultrasonic transmission and reception. A housing 6 encloses electrical connections between cable assembly 4 and acoustic module 2.

Figure 3:
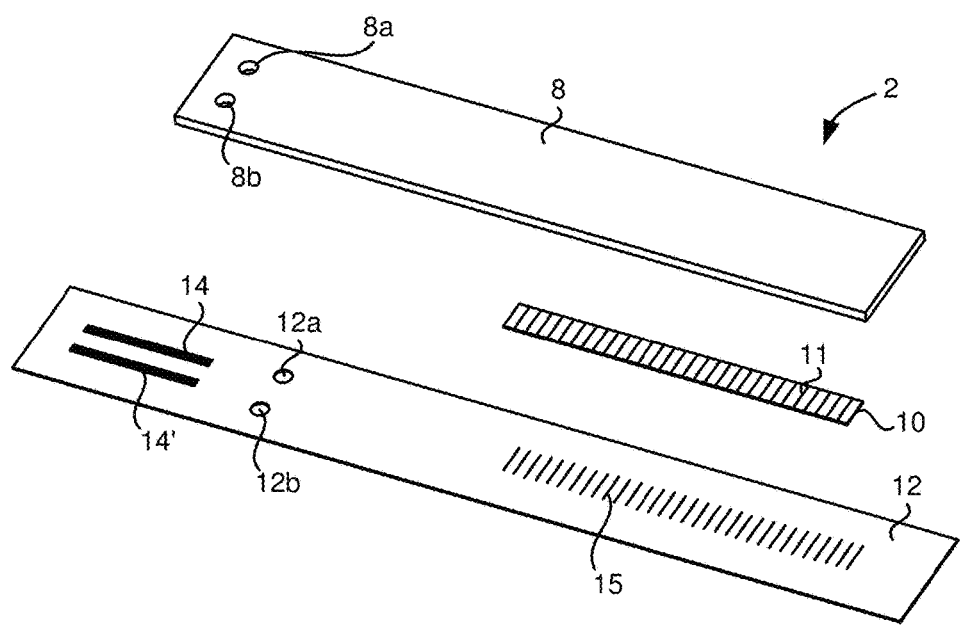
FIG. 3 is a diagram showing a first step in the assembly of a flexible probe array assembly according to the present disclosure.

FIG. 3 shows a first step in the assembly of flexible probe array assembly 1, which is bonding together of backing material 8, composite 10 and flexible circuit 12 to form acoustic module 2. Composite 10 comprises a piezoelectric material onto which a thin layer of conductive material is deposited on both sides. The conductive and piezoelectric materials are then scribed to produce an array of individual piezoelectric elements each with a conductive composite contact 11. In an embodiment, the piezoelectric material may be lead zirconium titanate (PZT), and the deposited conductive material may be gold. In a further embodiment, for illustrative purposes only, the composite may comprise a one dimensional array of 64 individual elements. However, it should be emphasized that the present invention is applicable to any type of composite.

Figure 6:
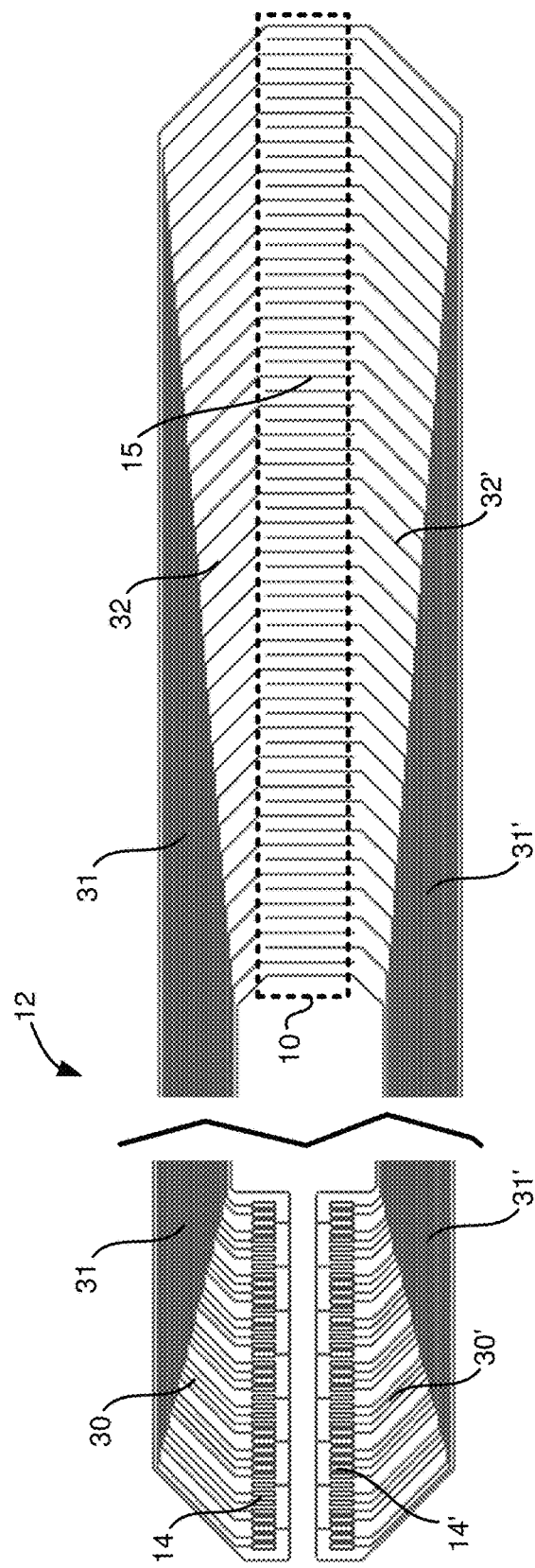
FIG. 6 is a circuit diagram of a flexible circuit according to the present disclosure.

Flexible circuit 12 is a flexible printed circuit board (PCB), in an embodiment made of polyimide material, upon which there are conductive traces whose purpose is to connect each of multiple connector contact pads 14 and 14' to a corresponding one of composite contact pads 15. The conductive traces are shown in more detail in FIG. 6, in which flexible circuit 12 is divided into two parts for convenience of display, it being understood that the two parts are in fact connected. As shown in FIG. 6, connector contact pads 14 are electrically connected to contact pad lines 30, which are connected to connecting lines 31, to composite contact lines 32 and finally to alternate composite contact pads 15. Similarly, connector contact pads 14' are electrically connected to contact pad lines 30', which are connected to connecting lines 31', to composite contact lines 32' and finally to alternate composite contact pads 15. In this way, each of connector contact pads 14 and 14' is electrically connected to a corresponding one of composite contact pads 15. The location of composite 10 after bonding to flexible circuit 12 is shown with a dotted line. In the view of FIG. 3, flexible circuit 12 is covered with a very thin non-conductive cover-lay material (not shown) in which two rectangular windows have been cut so that only connector contact pads 14 and 14' and composite contact pads 15 are exposed, and connecting lines 30, 30', 31, 31', 32, 32' are hidden.

Returning now to FIG. 3, the first step of the assembly is construction of acoustic module 2. Composite 10 is first bonded into a pocket (not shown) in backing material 8, and the combined composite 10 and backing material 8 is then bonded to flexible circuit 12 such that each composite contact 11 is aligned and in electrical contact with a corresponding composite contact pad 15. During the bonding, alignment holes 8a and 8b in backing material 8 are aligned with alignment holes 12a and 12b in flexible circuit 12. Bonding may be achieved with any suitable non-conductive bonding material such as non-conductive epoxy.

Figure 4:
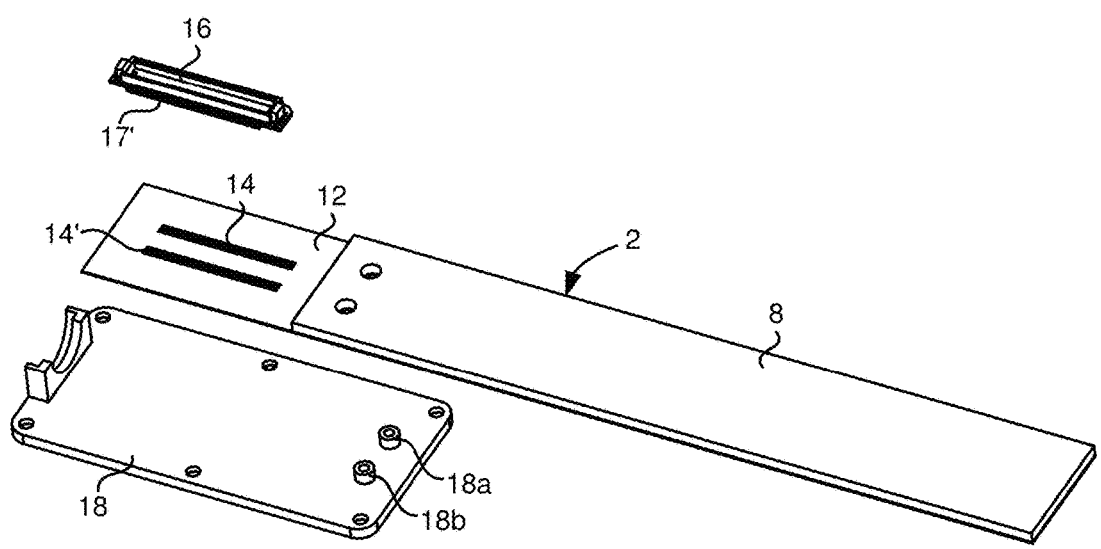
FIG. 4 is a diagram showing a second step in the assembly of a flexible probe array assembly according to the present disclosure.

FIG. 4 shows the second step of the assembly, in which acoustic module 2 is bonded to a base plate 18, with alignment achieved by means of a post 18a engaging with alignment holes 8a and 12a and a post 18b engaging with alignment holes 8b and 12b. Bonding may be achieved with any suitable bonding material such as epoxy. A connector 16 is then soldered to connector contact pads 14 and 14'. Connector 16 has a number of soldering pins 17 (not shown) and 17' configured so that each one of soldering pins 17 and 17' may be soldered to a corresponding one of connector contact pads 14 and 14'.

Figure 5A:
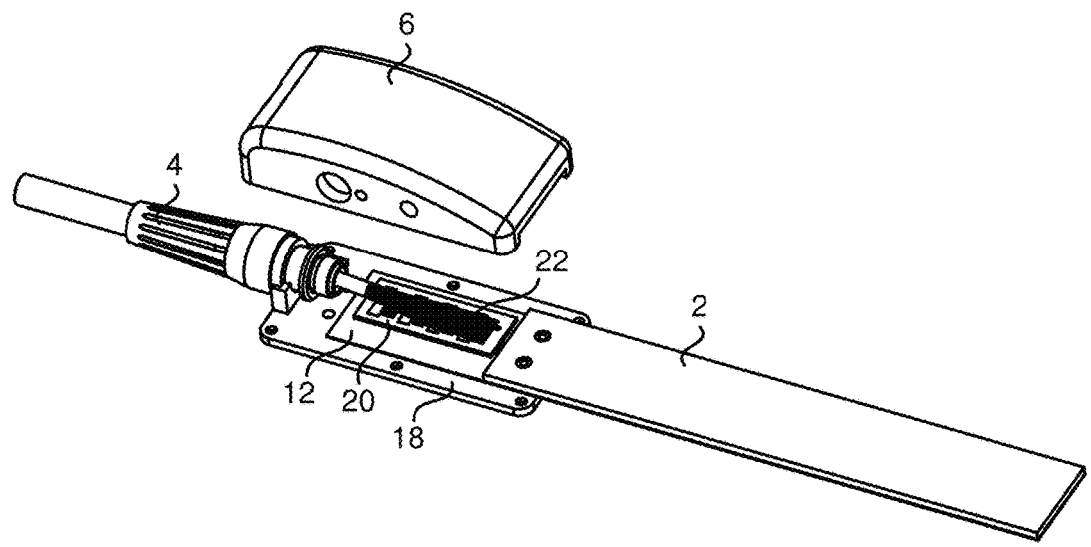
FIG. 5A is a diagram showing a third step in the assembly of a flexible probe array assembly according to the present disclosure.

In the third and final assembly step shown in FIG. 5A, a cable connecting printed circuit board (PCB) 20 is connected to flex circuit 12, and shielded conductors 22 of cable assembly 4 are soldered to pads on PCB 20. Finally, housing 6 is fixed with screws to baseplate 18, securely capturing cable assembly 4 and acoustic module 2.

Figure 5B:
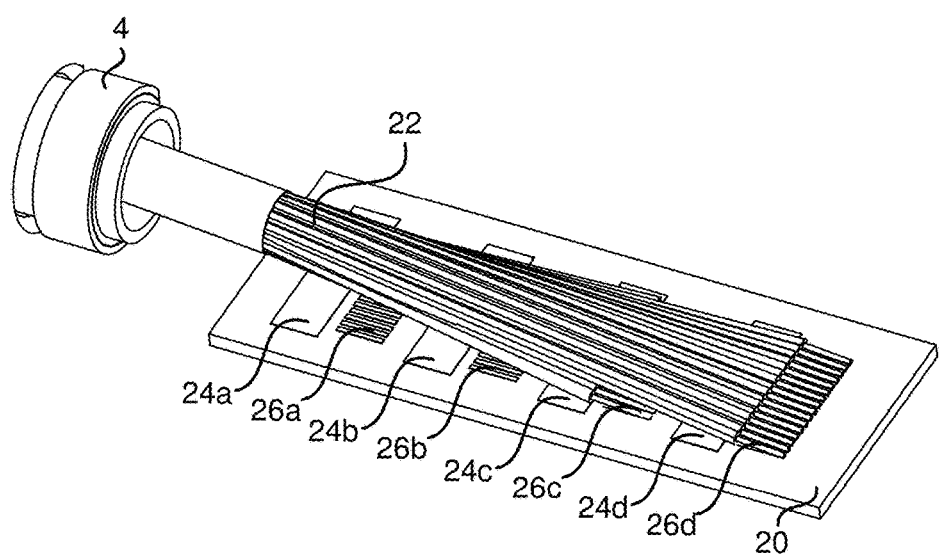
FIG. 5B is a diagram showing a detailed view of the third step in the assembly of a flexible probe array assembly according to the present disclosure.

FIG. 5B shows a more detailed view of cable connecting PCB 20 and cable assembly 4. PCB 20 comprises a bottom connector (not shown) on its bottom side, configured to connect electrically with connector 16 which is soldered to flexible circuit 12. PCB 20 routes the connections from the bottom connector to connection arrays 26a, 26b, 26c and 26d located on the top side of PCB 20. It should be noted that PCB 20 as illustrated has four connection arrays, each connection array having 16 connection pads, for a total of 64 connection pads suitable for the embodiment of a 64 element probe array. However, there may be any number of connection arrays, each having any number of connection pads suitable for a probe array having any number of elements, and all are within the scope of the invention. PCB 20 is also shown with four ground pads 24a, 24b, 24c and 24d located on the top side, but any number of ground pads is within the scope of the invention.

As shown in FIG. 5B, each of the conductors of shielded conductors 22 is soldered to a corresponding one of the connection pads in one of connection arrays 26a, 26b, 26c or 26d. At the same time, each of the shields of shielded conductors 22 is soldered to any one of ground pads 24a, 24b, 24c or 24d. The purpose of ground pads 24a, 24b, 24c and 24d is to ensure that all electrical signals are protected by a common ground.

The manufacturing method of the present invention is simplified and robust, and the resulting product has enhanced reliability and utility.

Although the present invention has been described in relation to particular embodiments thereof, it can be appreciated that various designs can be conceived based on the teachings of the present disclosure, and all are within the scope of the present disclosure.

What is claimed is:

1. An ultrasonic transducer configured to emit emitted ultrasonic energy and to receive corresponding reflected energy for inspecting a test object with a testing surface, the transducer having an active surface to be coupled with the testing surface during inspection, and the transducer having component layers comprising:
   a sheet of printed circuit board, of which one surface is either the active surface or is coated to be abutting the active surface, the other surface having at least one printed circuit printed thereon,
   a layer of piezoelectric ceramic composite having an emitting side and a non-emitting side, with the emitting side abutting the printed circuit board, and,
   a layer of backing material abutting the non-emitting side of the layer of ceramic composite, and
   wherein all the component layers are bonded together to form an acoustic laminated assembly in which the sheet of printed circuit board and the layer of piezoelectric ceramic composite are electrically connected, and the printed circuit board is further electrically coupled with at least one cable, and,
   wherein the printed circuit board is at least partially made of a material having acoustic impedance suitable to allow transmission of the emitted ultrasonic energy from the composite into the test object, and to substantially prevent undesirable reflected energy from transmitting back to the ceramic composite.

2. The ultrasonic transducer of claim 1 is a flexible ultrasonic phased array transducer, and,
   the sheet of printed circuit board is flexible,
   the layer of piezoelectric ceramic composite is flexible, and
   the layer of backing material is flexible.

3. The ultrasonic transducer of claim 1, wherein the printed circuit board is configured to function as a matching layer to allow efficient transmission of ultrasonic energy from the composite into the material being inspected, and to substantially prevent unwanted reflections so that the emitted ultrasonic energy can have shorter pulse width and larger bandwidth.

4. The ultrasonic transducer of claim 1 is a phased array transducer.

5. The ultrasonic transducer of claim 1, wherein the printed circuit board is made out of polyimide material.

6. The ultrasonic transducer of claim 1 wherein the printed circuit board is made out of material with acoustic impedance in the range from 2.5 to 7.5 MRayls.

7. The ultrasonic transducer of claim 6, wherein the printed circuit board is made out of material with acoustic impedance substantially close to 3.5 MRayls.

8. The ultrasonic transducer of claim 1 wherein the layer of piezoelectric ceramic composite is made of lead zirconium titanate.

9. The ultrasonic transducer of claim 4 wherein the layer of piezoelectric ceramic composite is scribed to produce an array of N piezoelectric elements, and an array of N conductive composite contacts is deposited on the emitting side, wherein each one of the array of N composite contacts makes electrical contact with a corresponding one of the array of N piezoelectric elements.

10. The ultrasonic transducer of claim 9 wherein the at least one printed circuit comprises an array of N composite contact pads, and wherein, in the acoustic laminated assembly, each one of the array of N composite contact pads makes electrical contact with a corresponding one of the array of N composite contacts.

11. The ultrasonic transducer of claim 10 wherein the at least one printed circuit further comprises an array of N connector contact pads and a number N of electrically conductive traces connecting each one of the array of N connector contact pads with a corresponding one of the array of N composite contact pads.

12. The ultrasonic transducer of claim 11 wherein a first multi-pin connector having an array of N soldering pins is soldered so that each one of the array of N soldering pins is soldered to a corresponding one of the array of N connector contact pads.

13. The ultrasonic transducer of claim 12 wherein a second multi-pin connector is connected to a cable connecting printed circuit board, and the second multi-pin connector connects with the first multi-pin connector.

14. The ultrasonic transducer of claim 13 wherein the second multi-pin connector has N cable connecting pins, and a cable connecting printed circuit board has N conducting cable connecting traces connecting each one of the N cable connecting pins to a corresponding one of an array of N cable connection pads.

15. The ultrasonic transducer of claim 14 wherein the at least one cable has an array of N shielded conductors, and each one of the array of N shielded conductors is soldered to a corresponding one of the array of N cable connection pads.

16. A method of providing and assembling an ultrasonic transducer having component layers and configured to emit emitted ultrasonic energy and to receive corresponding reflected energy for inspecting a test object with a testing surface, the transducer having an active surface to be coupled with the testing surface during inspection, the method comprising the steps of,
   providing a sheet of printed circuit board, of which one surface is the active surface, the other surface having at least one printed circuit printed thereon,
   providing a layer of piezoelectric ceramic composite having an emitting side and a non-emitting side, with the emitting side abutting the printed circuit board,
   providing a layer of backing material abutting the non-emitting side of the layer of ceramic composite, and,
   bonding all the component layers together in a stacked manner to form an acoustically laminated assembly in which the sheet of printed circuit board and the layer of piezoelectric ceramic composite are electrically connected, and the printed circuit board is further electrically coupled with at least one cable, and,
   wherein the printed circuit board is at least partially made of a material having a range of acoustic impedance suitable to allow transmission of the emitted ultrasonic energy from the composite into the test object, and to substantially prevent undesirable reflected energy from transmitting back to the ceramic composite.

17. The method of claim 16, wherein the printed circuit board is configured to function as a matching layer to allow efficient transmission of the emitted ultrasonic energy from the ceramic composite into the test object, and to substantially prevent unwanted reflections so that the emitted ultrasonic energy can have shorter pulse width and larger bandwidth.

18. The method of claim 17, wherein the printed circuit board is made out of polyimide material.

19. The method of claim 17 wherein the printed circuit board is made out of material with acoustic impedance in the range from 2.5 to 7.5 MRayls.

20. The method of claim 19, wherein the printed circuit board is made out of material with acoustic impedance substantially close to 3.5 MRayls.

21. The method of claim 16 wherein the layer of piezoelectric ceramic composite is made of lead zirconium titanate.

22. The method of claim 16, wherein the ultrasonic transducer is an ultrasonic phased array transducer.

* * * * *